US012728157B2

(12) United States Patent
Nilsson

(10) Patent No.: US 12,728,157 B2
(45) Date of Patent: Sep. 8, 2026

(54) AUTOLOGOUS CANCER TUMOUR ASSOCIATED EXTRACHROMOSOMAL CIRCULAR DNA FOR USE AS A THERAPEUTIC VACCINE

(71) Applicant: CIRCULAR BIOTECH AB, Umeå (SE)

(72) Inventor: Jonas Nilsson, Umeå (SE)

(73) Assignee: CIRCULAR BIOTECH AB, Umeå (SE)

( * ) Notice: Subject to any disclaimer, the term of this patent is extended or adjusted under 35 U.S.C. 154(b) by 924 days.

(21) Appl. No.: 17/426,002

(22) PCT Filed: Feb. 14, 2020

(86) PCT No.: PCT/SE2020/050169

§ 371 (c)(1),
(2) Date: Jul. 27, 2021

(87) PCT Pub. No.: WO2020/167240

PCT Pub. Date: Aug. 20, 2020

(65) Prior Publication Data

US 2022/0160850 A1 May 26, 2022

(30) Foreign Application Priority Data

Feb. 15, 2019 (SE) .................................. 1950187-3

(51) Int. Cl.
*A61K 39/00* (2006.01)
*A61P 35/00* (2006.01)

(52) U.S. Cl.
CPC .......... *A61K 39/0011* (2013.01); *A61P 35/00* (2018.01); *A61K 2039/53* (2013.01); *A61K 2039/55555* (2013.01); *A61K 2039/70* (2013.01)

(58) Field of Classification Search
CPC ............ A61K 39/0011; A61K 2039/53; A61K 2039/55555; A61K 2039/70; A61P 35/00
See application file for complete search history.

(56) References Cited

U.S. PATENT DOCUMENTS

| | | | |
|---|---|---|---|
| 2007/0160587 A1 | 7/2007 | Dobric et al. | |
| 2014/0178438 A1 | 6/2014 | Sahin et al. | |

FOREIGN PATENT DOCUMENTS

| | | | |
|---|---|---|---|
| CN | 1921882 A | 2/2007 | |
| CN | 103608033 A | 2/2014 | |
| CN | 105999250 A | 10/2016 | |
| WO | WO-9739149 A1 * | 10/1997 | .............. C12Q 1/68 |

OTHER PUBLICATIONS

Turner et al. Extrachromosomal oncogene amplification drives tumor evolution and genetic heterogeneity. Nature. Mar. 2, 2017; 543(7643): 122-125 (Year: 2017).*

Moller et al. Circular DNA elements of chromosomal origin are common in healthy human somatic tissue. Nature Communications (2018) 9:1069, p. 1-12 (Year: 2018).*

Moller et al. Genome-wide Purification of Extrachromosomal Circular DNA from Eukaryotic Cells. J. Vis. Exp. (110), e54239, p. 1-8 (Year: 2016).*

Kumar et al. Normal and Cancerous Tissues Release Extrachromosomal Circular DNA (eccDNA) into the Circulation. Mol Cancer Res; 15(9); 1197-205 (Year: 2017).*

Walters et al. A Novel DNA Vaccine Platform Enhances Neo-antigen-like T Cell Responses against WT1 to Break Tolerance and Induce Anti-tumor Immunity. Molecular Therapy vol. 25 No. 4 Apr. 2017, p. 976-988 (Year: 2017).*

Lopes et al. Combination of immune checkpoint blockade with DNA cancer vaccine induces potent antitumor immunity against P815 mastocytoma. Scientific Reports. 8:15732, p. 1-11 (Year: 2018).*

DeCarvalho et al. Discordant inheritance of chromosomal and extrachromosomal DNA elements contributes to dynamic disease evolution in glioblastoma. Nature Genetics. vol. 50, 708:708-717 (Year: 2018).*

Zhao et al. Nanoparticle vaccines. Vaccine 32 (2014) 327-337 (Year: 2014).*

Halpern. Proto-oncogene products as target antigens for cancer vaccines (Review). International Journal of Oncology II: 863-868 (Year: 1997).*

Lai et al. The effects of DNA formulation and administration route on cancer therapeutic efficacy with xenogenic EGFR DNA vaccine in a lung cancer animal model. Genetic Vaccines and Therapy 2009, 7:2, p. 1-13 (Year: 2009).*

Steinman et al. Dendritic Cells: Important Adjuvants During DNA Vaccination. Madame Curie Bioscience Database [Internet]. Austin (TX): Landes Bioscience; 2000-2013, p. 1-25 (Year: 2013).*

Aurisicchio et al., "Poly-specific neoantigen-targeted cancer vaccines delay patient derived tumor growth", Journal of Experimental & Clinical Cancer Research, 2019, vol. 38, No. 78, XP055694082, total 13 pages.

International Search Report, issued in PCT/SE2020/050169, dated May 26, 2020.

Khatami et al., "The presence of tumor extrachomosomal circular DNA (ecDNA) as a component of liquid biopsy in blood", Medical Hypotheses, 2018, vol. 114, XP085368386, pp. 5-7.

Nathanson et al., "Targeted Therapy Resistance Mediated by Dynamic Regulation of Extrachromosomal Mutant EGFR DNA", Science, Jan. 3, 2014, vol. 343, XP002780080, pp. 72-76.

Von Hoff et al., "Hydroxyurea Accelerates Loss of Extrachromosomally Amplified Genes From Tumor Cells", Cancer Research, Dec. 1, 1991, vol. 51, XP002917532, pp. 6273-6279.

Written Opinion of the International Searching Authority, issued in PCT/SE2020/050169, dated May 26, 2020.

(Continued)

*Primary Examiner* — Taeyoon Kim

(74) *Attorney, Agent, or Firm* — Birch, Stewart, Kolasch & Birch, LLP

(57) ABSTRACT

Autologous cancer tumour associated extrachromosomal circular DNA (ecDNA) for use as a therapeutic vaccine against the cancer, and methods for preparing an autologous therapeutic vaccine.

5 Claims, 3 Drawing Sheets

(56) References Cited

OTHER PUBLICATIONS

Biedler & Spengler, "A novel chromosome abnormality in human neuroblastoma and antifolate-resistant Chinese hamster cell lines in culture," J. Natl. Cancer Inst., vol. 57, No. 3, Sep. 1976, pp. 683-695.

Stephens et al., "Massive genomic rearrangement acquired in a single catastrophic event during cancer development," Cell 144, Jan. 7, 2021, pp. 27-40.

Veerhak et al., "Extrachromosomal oncogene amplification in tumour pathogenesis and evolution," Nat RevCancer, 19(5): May 2019, pp. 283-288.

Gubin et al., "Tumor neoantigens: building a framework for personalized cancer immunotherapy." Journal of Clinical Investigation, vol. 125, No. 9, 2015, pp. 3413-3421.

Hanahan, "Hallmarks of Cancer: New Dimensions," Cancer Discovery, 2022, pp. 31-46.

Oshita et al., "Dendritic cell-based vaccination in metastatic melanoma patients: Phase II clinical trial," Oncology Reports, vol. 28, 2012, pp. 1131-1138.

* cited by examiner

AUTOLOGOUS CANCER TUMOUR ASSOCIATED EXTRACHROMOSOMAL CIRCULAR DNA FOR USE AS A THERAPEUTIC VACCINE

TECHNICAL FIELD

The disclosure is related to an autologous cancer tumour associated extrachromosomal circular DNA (ecDNA) for use as a therapeutic vaccine against the cancer. The disclosure is also related to methods for production of such a vaccine.

BACKGROUND

Cancer is a generic term for a large group of diseases characterized by the growth of abnormal cells beyond their usual boundaries, which cells can invade adjoining parts of the body and/or spread to other organs in the body.

The adaptive immune response, mediated by antibody-producing B cells and cytotoxic T cells, protects us from disease by killing invading pathogens and performing immune surveillance to eliminate tumours prior to metastasis. To avoid killing of "self" and induction of severe autoimmunity, cells of the adaptive immune system undergo a stringent selection process during their development, where self-reactive cells are eliminated.

In cancer patients the immune system is already activated, but the immune response can either be to week, too few neoantigens are present that can elicit an immune response, or the tumour has suppressed the immune system by expression of cytokines (e.g. TGF-B, etc) or molecules that deactivate the immune response (e.g. cell surface expressed Program Death-Ligand 1 (PDL1)).

Therapeutic vaccines may be used in cancer treatment to elicit a stronger immune response and to alter the quality of the immune response, i.e. causing a reprogramming of the immune system. To activate the immune system the vaccine antigen need to be presented to the immune system in such a way that it is considered a risk (e.g. have a T-cell repertoire that recognise the antigen) for the individual, such as to kick-start the immune system.

A majority of human tumours, 80-85 percent, is considered not to be induced by virus or bacteria. Tumour antigens on the cancer cells, as compared to foreign antigens on bacteria and virus, are often endogenous proteins. The immune system has developed efficient mechanisms to prevent the autoimmunity, which an immune reaction against endogenous tumour antigens means. It is, hence, a challenge to provide therapeutic vaccines against cancer forms not induced by bacteria or virus.

As of today, there has not yet been a real break-through in the use of therapeutic cancer vaccines. Using full genome, cellular material or cell lysates for vaccination has not been fully successful. Using vaccines of tumour cell lysates (containing all components, protein, DNA etc.) has shown to elicit a quite weak immune response. One problem with using full genome material, cellular material or cell lysates is that it contains more than 99.9% of normal information regarding DNA alterations, expressed protein epitopes for immune recognition etc. More than 99.9% of everything that is exposed to the immune system when using a full genome vaccine is normal and prevent activation against something that is altered. Mainly by over-loading the MHCI/II complexes with antigen peptides derived from normal proteins, T-cells are negatively selected already during T-cell maturation.

Furthermore, during maturation of immune cells there is a negative selection of cells that recognize self-antigens. The immune system has two issues to deal with; overload of normal epitopes to display, and few immune cells having a possibility to recognize altered epitopes with close homology to endogenous normal expressed protein epitopes. The full genome material, cellular material or cell lysates contain a few neo-antigens, antigens encoded by tumour-specific mutated genes in comparison to antigens from normal proteins.

Activating the immune system in this way results in an overload of the antigen presenting system, where the antigen presenting cells, APCs, which activate the immune system only produces antigenic peptides of limited/no antitumor activity.

Hence, there is a need for more effective vaccines for the treatment of cancer.

SUMMARY

An object of the present invention is to provide an autologous cancer tumour associated extrachromosomal circular DNA (ecDNA) for use as a therapeutic vaccine against the cancer. Such cancer vaccine overcomes at least some of the drawbacks with cancer vaccines based on full genome material, cellular material or cell lysates. A further objective is to provide methods for producing such a vaccine.

The invention is defined by the appended independent claims. Embodiments are set forth in the appended dependent claims and in the figures.

According to a first aspect there is provided an autologous cancer tumour associated extrachromosomal circular DNA (ecDNA) for use as a therapeutic vaccine against the cancer. According to another aspect, the ecDNA is enriched from a sample by an enzymatic treatment or digestion of DNA. The enzymatic treatment or digestion may comprise at least one enzyme selected from exonucleases and endonucleases. The enzymatic treatment or digestion may comprise at least one exonuclease. Such exonucleases and endonucleases are known in the art.

A sample may be defined as any matter obtainable from the human or animal body and may comprise tumour DNA, such as tumour cells, tumour tissue, blood, urine, serum or plasma, Extrachromosomal circular DNA, ecDNA, which propagates along the chromosomes during cell divisions, has been shown to carry a majority of the amplified epidermal growth factor receptor (EGFR) locus and EGFRvIII-mutants seen in glioblastoma (GBM). Tumour tissue carry more ecDNA than normal tissue. Any ecDNA pool may only consist of a 1/1.000-100.000 part of the full genome (the human genome consisting of more than $6.4\times10^9$ bases (diploid genome). Selected regions can be amplified at very large numbers, and as many as 100 copies can be seen within an individual GBM tumour cell for the EGFR and EGFRvIII-mutation locus. For ecDNA to be present and selectively kept in the genome of a cancer cell there need to be a selection pressure from the DNA residing in those ecDNA fragments providing a growth advantage. EcDNA is, however, not necessary for growth per se.

EcDNA provides an enriched neoantigen source that can be more than 1.000 times enriched compared to the full genome, where a selected ecDNA region (ex size: 1/100.000 of a the full human genome) x genome amplification (10-100 times) can results in a more than 1.000 times enrichment of those regions compared to the full normal genome.

When using autologous cancer tumour associated ecDNA as a personalized therapeutic vaccine a highly enriched fraction of relevant (in vivo selection pressure) neoantigens is displayed for the immune system and therefore a more potent immune reaction is elicited compared to whole genome vaccination. Tumour derived ecDNA carry unique information that is masked in an undigested sample analysis, as normal linear DNA both from normal cells as well as tumour cells mask the ecDNA signature, and thereby the tumour specific information carried in ecDNA. Tumour derived ecDNA may be obtained by growing tumour cells as organoids or spheroids to expand the number of tumour cells before extraction.

An autologous cancer tumour associated ecDNA is derived from the very same cancer against which it is used as a personalized therapeutic vaccine.

With tumour associated is here meant that the ecDNA is derived directly from cancer cells. Alternatively, the ecDNA may be derived from a liquid biopsy, e.g. a sample of blood, urine, serum or plasma, comprising circulating free ecDNA from the cancer tumour.

Autologous cancer tumour associated ecDNA may be used as a therapeutic vaccine in humans or mammals.

The cancer may be selected from a group comprising prostate cancer, breast cancer, colon cancer, lung cancer, liver cancer, pancreatic cancer, skin cancer and brain cancer.

The autologous cancer tumour associated ecDNA may be used as a vaccine together with a pharmaceutically acceptable adjuvant or excipient.

The adjuvant/excipient may help create a stronger immune response in the patient's body. Such adjuvants/excipients are known in the art.

According to a second aspect there is provided a therapeutic cancer vaccine comprising autologous cancer tumour associated ecDNA as described above.

According to a third aspect there is provided a method of preparing an autologous therapeutic cancer vaccine, comprising: extracting and isolating total DNA content from tumour cells from a tumour tissue, and enriching cancer tumour associated extrachromosomal circular DNA (ecDNA) from the extracted DNA by enzyme digestion of linear DNA.

According to fourth aspect there is provided a method of preparing an autologous therapeutic cancer vaccine, comprising: extracting and isolating circulating free DNA from blood, urine, serum or plasma, and enriching cancer tumour associated extrachromosomal circular DNA (ecDNA) from the extracted DNA by enzyme digestion of linear DNA.

Circulating free DNA (cfDNA) are mainly degraded DNA fragments released to the blood plasma. CfDNA can be used to describe various forms of DNA freely circulating the bloodstream, including ecDNA. CfDNA are observed in cancer, especially in advanced disease. EcDNA released into circulation is more stable sbeing circular) than other circulating free DNA, why it is possible to enrich ecDNA with linear degrading nucleases. By isolation from a liquid biopsy source, blood, urine, serum, plasma, it is possible to enrich for both mutations and amplifications as well as for transcriptional activity occurring in tumour cells.

The methods may further comprise a step of amplifying the enriched ecDNA.

Amplification may take place for example by rolling circle amplification using phi29 polymerase.

Through such amplification it is possible to generate a large enough quantity of ecDNA to enable repeated vaccinations.

The methods described may further comprise a step where the enriched ecDNA is sequenced and each ecDNA molecule is "de novo"-assembled to elucidate their genomic structure.

Matched RNA is sequenced to identify RNA molecules uniquely transcribed from ecDNA molecules.

Genetic alterations identified from the combined DNA and RNA sequencing may be combined synthetically into nucleic acid molecules that produce at least one ecDNA derived genetic alteration that can be presented to the immune system. According to one aspect, a the therapeutic cancer vaccine for use in a method of treating cancer comprises a synthesized nucleic acid obtainable from an ecDNA derived RNA sequence, at least one of pharmaceutically acceptable component selected from buffers, salts, preservatives, carriers, adjuvants and saponins, wherein the synthesized nucleic acid comprises a tumour associated extrachromosomal circular DNA (ecDNA) comprising at least one genetic alteration with potential to elicit an immune response.

A genetic alteration may be a mutation, insertion or deletion within the DNA or a genomic rearrangement, resulting in amino acid changes, frame-shift alterations or new fusion genes.

At least a portion of the enriched ecDNA may be bound nanoparticles selected from polymer particles, lipid particles and liposome particles, or peptide-based delivery modalities or microparticles selected from gold or tungsten microparticles.

The methods may further comprise a step of delivering the ecDNA to autologous antigen presenting cells ex vivo.

Such antigen presenting cell, APC, transfected with ecDNA may transcribe and translate neoantigen proteins from the ecDNA and display them on the MHC-I complexes of the APCs. The APCs may be isolated from the same patient as the ecDNA is derived from.

The antigen presenting cells may be dendritic cells. The antigen presenting cells may comprise macrophages, B lymphocytes. T lymphocytes or any nucleated cell type.

According to a fifth aspect there is provided an autologous therapeutic cancer vaccine produced in accordance with any of the methods described above, which vaccine may be administered intradermally or intravenously or directly to the lymphatic system, preferably to at least one lymph node or proximity of lymph node.

The autologous therapeutic cancer vaccine produced in accordance with any of the methods described above may be contacted to the lymphatic system, preferably to at least one lymph node or proximity of lymph node.

EcDNA may be administered to a patient directly after vaccine preparation, wherein the vaccine is taken up by APCs and display neoantigen proteins from the ecDNA on its MHC-I or MHC-II complexes.

The ex vivo transfected APCs may be reinserted into the patient to activate the immune system, i.e. cell-based therapy.

According to another aspect there is provided a method of preparing an autologous therapeutic cancer vaccine, comprising extracting total DNA content from tumour cells, and enriching cancer tumour associated extrachromosomal circular DNA (ecDNA) from the extracted DNA.

According another aspect there is provided a method of preparing an autologous therapeutic cancer vaccine, comprising extracting circulating free DNA from blood, urine, serum or plasma, and enriching cancer tumour associated extrachromosomal circular DNA (ecDNA) from the extracted DNA.

According to another aspect, the method of preparing an autologous therapeutic cancer vaccine may further comprise combining the ecDNA with at least one of pharmaceutically acceptable component selected from buffers, salts, preservatives, carriers, adjuvants and saponins.

According to another aspect, the method of preparing an autologous therapeutic cancer vaccine further comprises DNA sequencing of the enriched DNA, RNA sequencing of RNA molecules and identifying RNA sequences transcribed from tumour associated ecDNA and combining at least one tumour associated ecDNA expressing RNA with at least one pharmaceutically acceptable component. The DNA and RNA sequencing may be important to identify RNA sequences transcribed from tumour associated ecDNA, which allows the preparation of a cancer vaccine having specific ecDNA sequences able to be transcribed into RNA and translated into proteins.

A therapeutic cancer vaccine for use in a method of treating cancer may comprise at least one extrachromosomal circular DNA (ecDNA) and at least one of pharmaceutically acceptable component selected from buffers, salts, preservatives, carriers, adjuvants and saponins, wherein the at least one extrachromosomal circular DNA (ecDNA) may comprise a tumour associated ecDNA.

According to another aspect, a therapeutic cancer vaccine for use in a method of treating cancer may comprise a synthesized nucleic acid obtainable from an ecDNA derived RNA sequence and at least one of pharmaceutically acceptable component selected from buffers, salts, preservatives, carriers, adjuvants and saponins. According to one aspect, the synthesized nucleic acid comprises a tumour associated extrachromosomal circular DNA (ecDNA) comprising at least one genetic alteration with potential to elicit an immune response.

According to another aspect, the therapeutic cancer vaccine for use in a method of treating cancer may comprise the autologous tumour associated ecDNA according to any of the previous embodiments and obtainable by any of the previous embodiments.

According to the present invention, the term vaccine refers to a pharmaceutical composition that induces an immune response. The immune response therefore recognizes and attacks disease cells such as pathogens or tumour cells. Vaccines can be used to prevent or treat disease.

DETAILED DESCRIPTION

Figure 1:
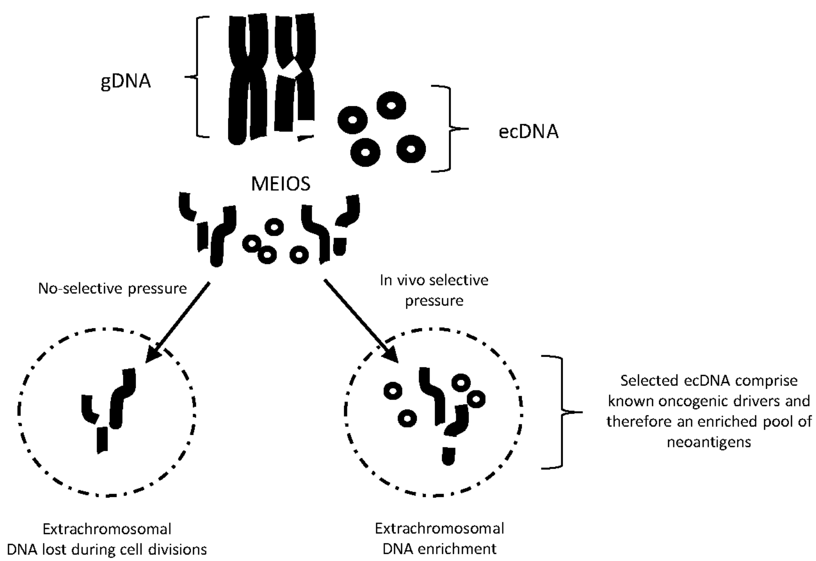
FIG. 1 illustrates extrachromosomal circular DNA enrichment in cancer.

Circular extrachromosomal DNA (ecDNA)/satellite DNA/dmin) has been known for several decades. Extrachromosomal circular DNA, ecDNA, is not part of the chromosomes but can propagate along the chromosomes during cell divisions. EcDNA has been shown to carry a majority of the amplified epidermal growth factor receptor (EGFR) locus and EGFRvIII-mutants seen in glioblastoma (GBM). EcDNA is under selective pressure (Schulte et al. (2012). *Glioblastoma Stem-like Cell Lines with Either Maintenance or Loss of High-Level EGFR Amplification, Generated via Modulation of Ligand Concentration*. Clinical Cancer Research 18, 1901-1913.) and when co-segregating with the chromosomes during cell division, the cells that retain ecDNA have a growth advantage in a hostile microenvironment. Cells with amplified ecDNA are more protected than corresponding tumour cells without ecDNA (see FIG. 1). The more amplifications the more protection, and as many as 100 copies can be seen within an individual GBM tumour cell for the EGFR and EGFRvIII-mutation locus. EcDNA is, hence, not necessary for growth per se, but in a patient's tumour (hostile tumour microenvironment) it protects the cells from dying and provide growth advantage over non-ecDNA carrying tumor cells (deCarvalho et al. (2018). *Discordant inheritance of chromosomal and extrachromosomal DNA elements contributes to dynamic disease evolution in glioblastoma*. Nature Genetics 50, 708-717.). As ecDNA is replicated during S-phase, but lack centromeres that dictate the organisation of the mitotic spindle, ecDNA is randomly distributed across the daughter cells during mitosis and lost by dilution when the selection pressure is removed.

EcDNA can be divided into two main categories, small respective large ecDNA molecules. The small ones (100-400 nt) can be attributed to high transcriptional turnover (Dillon et al. (2015). *Production of Extrachromosomal MicroDNAs Is Linked to Mismatch Repair Pathways and Transcriptional Activity*. Cell Reports 11, 1749-1759.) whereas the larger ones seem to accumulate in cancer part of a selection process. Both types can be linked to repair mechanism of the DNA and therefore increase in cancer cells that often show a deregulated DNA damage response (DDR).

The human genome consists of more than $6.4\times10^9$ bases (diploid genome) and any ecDNA pool may only consists of about a 1/1.000 part of the genome, but selected regions can be amplified at very large numbers (>100 times EGFRvIII mutants on dmin). For ecDNA to be present and selectively kept in the genome of a cancer cell there needs to be a selective benefit from the DNA residing in those ecDNA fragments providing a growth advantage (important function for the tumour), i.e. there is a selection pressure. The ecDNA is not densely packed (like heterochromatin) instead it has the potential to be very active in transcription and have less restrictions of epigenetic silencing. EcDNA provides an enriched neoantigen source tha can be more than 1.000.000 times enriched compared to the full genome. Selected ecDNA regions (size: 1/1.000-1/100.000 of a full human genome)×genome amplification (10-100 times) results in more than 10.000 times enrichment of those regions compared to a full normal genome. EcDNA has the potential to display a highly enriched fraction of relevant (in vivo selection pressure) neoantigens to antigen presenting cells (APCs) such as dendritic cells. Used as a cancer vaccine, ecDNA therefore provide a more potent immune reaction compared to whole genome vaccination. Compared to vector-based DNA-vaccines, which only contain one or a few possible neoantigens, the use of ecDNA as a cancer vaccine provides an in vivo selected repertoire of potentially active neoantigens. Therefore, the ecDNA provide an enriched source of positively selected tumour-derived genomic information, hence ecDNA express a broad display of tumour-derived transcripts, translating novel peptides with neoantigenic properties.

There is an enrichment of tumour derived ecDNA that carry unique information that is masked in an undigested sample analysis, as normal linear DNA both from normal cells as well as tumour cells mask the ecDNA signature, and thereby the tumour specific information carried in ecDNA. Using autologous ecDNA a personalized disruptive pan-cancer liquid vaccination platform is provided. The enrichment procedure unmasks the neoantigens from normal translated proteins by increasing the ratio of neoantigens eliciting an immune response from normal antigens that can be displayed on MHC-I/II complexes for the immune system.

Figure 2:
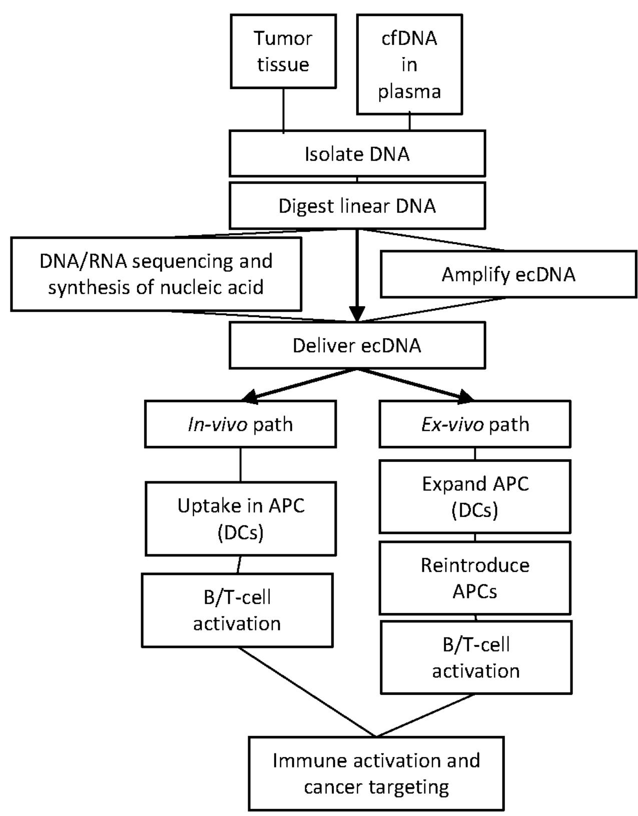
FIG. 2 shows a method scheme for production of an autologous therapeutic cancer vaccine comprising autologous cancer tumour associated extrachromosomal circular DNA (ecDNA) and use thereof for immune activation.

Below follows a general procedure for production of autologous ecDNA for use as a vaccine, which is also schematically illustrated in FIG. 2 and FIG. 3.

Isolation, Extraction and Enrichment of ecDNA

EcDNA from cancer tumour cells can be isolated in different ways. As the ecDNA molecules have similarities with large DNA plasm ids, it is possible to isolate and enrich ecDNA molecules with standard plasmid isolation kits (e.g. large construct kit, Qiagen).

Another approach is to use pulsed field gel electrophoresis (PFGE) to be able to separate chromosomal, linear DNA from ecDNA. Pulsed field gel electrophoresis (PFGE) technique is known in the art.

Another approach is to use density centrifugation methods (Radloff et al 1967 (PNAS)) together with DNA intercalating molecules (like ethidium bromide) to separate linear DNA from circular DNA. Combining centrifugation and DNA intercalating molecules is known in the art.

The isolated DNA will still contain some linear DNA, which may be removed with nucleases that target linear dsDNA (e.g. Exonuclease V). The final pool of ecDNA may be cleaned by standard methods (e.g. precipitation, bead, column-based methods).

From a liquid biopsy (serum, plasma, blood, urine) ecDNA may be isolated together with circulating free DNA, cfDNA, in the sample. The cfDNA comes mainly from chromosomal DNA that is wrapped around nucleosomes and fragmented and is, hence linear, during normal cell death. The linear cfDNA can be digested with nucleases as described above.

Characterisation of ecDNA from tumours has shown that ecDNA as big as 800 kbp genomic regions contain known oncogenes, see e.g. Sandberg et al. (2013). *Double Minute Chromosomes in Glioblastoma Multiforme Are Revealed by Precise Reconstruction of Oncogenic Amplicons Cancer Res;* 73(19) and deCarvalho et al. (2018). *Discordant inheritance of chromosomal and extrachromosomal DNA elements contributes to dynamic disease evolution in glioblastoma.* Nature Genetics 50, 708-717. Both publications show genetic rearrangements found in the TCGA-database that lead to ecDNA accumulation of known oncogenic drivers in gliomas, where up to 60% of the manually curated ecDNA were belonging to known oncogenes.

Amplification of Isolated and Extracted ecDNA

Expansion of the enriched ecDNA pool can be done by rolling circle amplification with a strand displacement active polymerase with high fidelity, like phi29 DNA polymerase. This may be followed by T7 nuclease digestion of hyper branched amplification products to yield an amplified pool of the ecDNA. Impurities from the amplification and digestion will be removed by a DNA clean-up step, by for example using precipitation or column-based methods, before the ecDNA can be used as a substrate of the vaccine. Through such amplification it is possible to generate a large enough quantity of ecDNA to enable repeated vaccinations from a low yield biosource as for example plasma or a fine needle biopsy.

Synthetically Produce Nucleic Acid Products Tanscribed from ecDNA Mlecules

The enriched ecDNA, with or without amplification, is sequenced using known-in-the-art techniques (like sequence by synthesis (Illumina Inc.) or nanopore sequencing (Oxford Nanopore Inc.)). The generated sequencing reads are used to assemble the ecDNA genomic structure based on genomic breakpoints within the ecDNA molecules. Matched RNA samples are sequenced and mapped against the ecDNA molecules finding RNA molecules translating novel amino acid compositions that are normally not expressed and translated. The genetic alterations identified by the combined DNA and RNA sequencing may be combined synthetically into nucleic acid molecules that produce at least one ecDNA derived genetic alteration that can be translated and presented to the immune system. Genetic alterations can be added in tandem using a common read-frame that will translate each alteration into a combined peptide. A genetic alteration may be a mutation, insertion or deletion within the DNA or structural genomic rearrangement, resulting in amino acid changes and neoantigen formation.

Preparation of Vaccine Comprising the ecDNA

In addition to the isolated and extracted (and possibly also amplified) ecDNA, the vaccine may comprise pharmaceutical excipients known in the art (see for example Rowe R C et al., Handbook of Pharmaceutical Excipients. Pharmaceutical Press, 2012., or Wen E P et al., Vaccine Development and Manufacturing, John Wiley & Sons, 17 Nov. 2014). Preservatives, adjuvants, stabilizers and buffers are non-restricted examples of excipients that may be used.

Preservatives may be used to prevent growth of bacteria or fungi that may be introduced into the vaccine during its use, for example by repeated puncture of a multi-dose vaccine vial with a needle.

Adjuvants may help stimulating a stronger immune response of vaccinated individuals. Aluminium salts may be incorporated into a vaccine formulation as an adjuvant. Examples of aluminium salts are aluminium hydroxide, aluminium phosphate, alum (potassium aluminium sulphate), or mixed aluminium salts. Organic compounds such as squalene or oil-based compounds may also be used as adjuvant.

Stabilizers may keep vaccines potent during transportation and storage. They help protect the vaccine from adverse conditions such as the freeze-drying process, for those vaccines that are freeze dried. Some examples of stabilizers which may be added to vaccines include; sugars such as sucrose and lactose, amino acids such as glycine or the monosodium salt of glutamic acid and proteins such as human serum albumin or gelatine.

Delivery of ecDNA to Antigen Presenting Cells, APCs, Ex Vivo, Transfection

The delivery of the patients ecDNA vaccine to his/her own isolated APCs, e.g. dendritic cells, is similar to ex vivo plasmid-based DNA delivery to APCs used today. The ecDNA can be delivered to autologous APCs ex vivo as naked ecDNA. Alternatively, electroporation of the cells with ecDNA may be performed. Another approach is to use nanoparticles that can be loaded with ecDNA, which may allow for a controlled, specific cell/site targeting release of DNA load. The nanoparticles may be made of polymer particles, lipids particles, liposome particles, or peptides-based delivery modalities. These techniques can be used in combination with additional adjuvants (e.g. GM-CSF (granulocyte/macrophage-colony stimulating factor), etc.) to promote and strengthen an adaptive immune response.

Delivery of Vaccine or Transfected APCs to Patient

The delivery of ecDNA vaccine to a patient is similar to plasmid-based DNA delivery to APCs used today. The ecDNA can be injected in the patient intramuscularly, intradermally, near lymph nodes etc. as naked ecDNA. The ecDNA is then taken up by professional APCs in vivo or cross-presented to the APCs. A second approach is to use the so-called gene gun, wherein ecDNA is bound to metal microparticles (e.g. gold or tungsten). The ecDNA-microparticles are shot through the skin for ecDNA uptake and antigen presentation in APCs. Yet another variant is to use nanoparticles that can be loaded with ecDNA, which can allow for a controlled, specific cell/site targeting release of DNA load. The nanoparticles can be polymer particles, lipid particles, liposome particles, or peptides-based delivery modalities. These techniques can be used in combination with additional adjuvants (e.g. GM-CSF (granulocyte/macrophage-colony stimulating factor), etc.) to promote and strengthen an adaptive immune response.

The delivery method determines the dose required to raise an effective immune response. A vaccine dose may comprise 0.1 μg-1 mg ecDNA. Vaccination may be repeated for example 2-3-times every other or third week.

Ex vivo matured APCs transfected with ecDNA may be administered to the patient. These administrations can range for up to three biweekly vaccinations, followed by up to 10 booster vaccinations at 2-6-month intervals.

Proof of Principle

From a patient with castration-resistant prostate cancer, circulating free (cf)-DNA was isolated according to general protocols (e.g. Circulating Nucleic Acid kit, Qiagen). After isolation, cfDNA was subjected to linear DNA digestion using an enzyme digesting linear DNA, like Exonuclease V (e.g. Plasm id-safe ATP-dependent kit (Epicenter)). If the DNA is protected by circularization, e.g. ecDNA, the copy numbers measured with digital droplet polymerase chain reaction (ddPCR, Bio-Rad) will increase compared to the control region located within a known stable genomic region not implicated in cancer. The commonly amplified AR (androgen receptor) gene in prostate cancer was compared with a genomic stable region in CYP1B (cytochrome 450).

Figure 3:
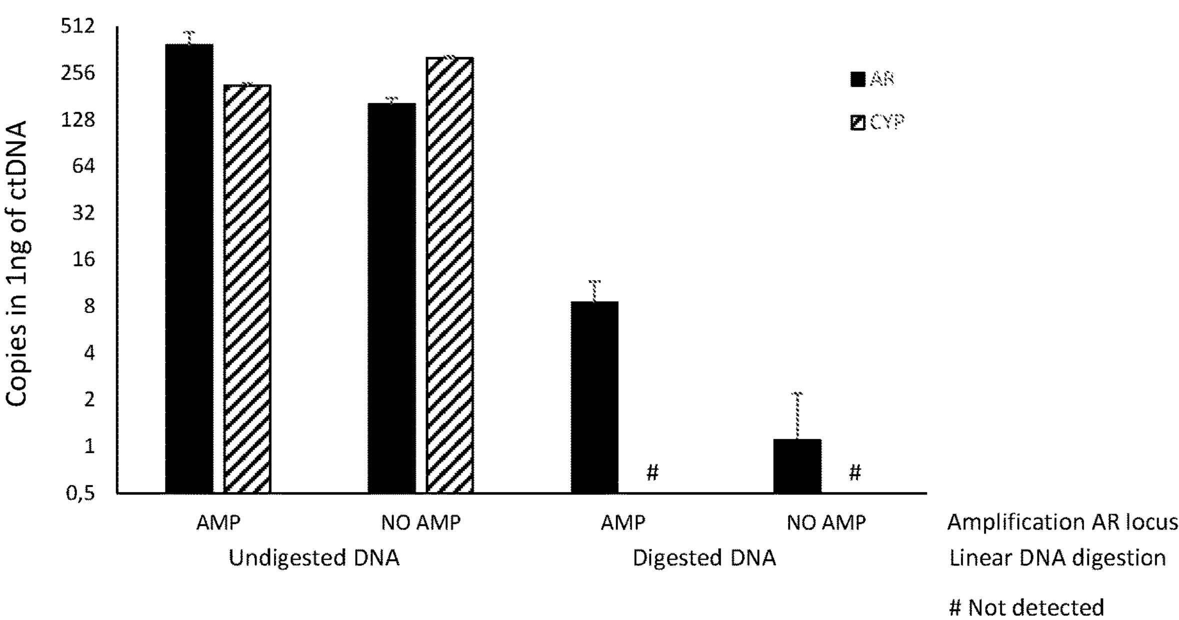
FIG. 3 is a graph showing proof-of-concept that tumour derived information is protected in ecDNA.

In FIG. 3 the results from such a test are illustrated. To the left is shown the copy numbers of AR and CYP1B samples, respectively, without linear DNA digestion. To the right is shown the copy numbers of AR and CYP1B samples treated with linear DNA digestion. Copy numbers were analyzed in patients with either confirmed gain of AR (AMP) or with normal AR copy numbers (NO AMP). It was seen that 1-2% of AR copies are protected against digestion, both in tumours with amplified (AMP) AR (2% protected), as well as in tumours with normal (NO AMP) AR copy levels (~1% protected). Simultaneously the genomic stable region did not show the same protection (not detected, #), indicating that many AR receptor loci are located in protected ecDNA in plasma. Also, that amplification/gain negative patients have some gain in ecDNA loci of known oncogenes, indicating that enrichment of ecDNA by digesting linear DNA increase the sensitivity to find tumour information within the blood circulation.

This proof-of-concept shows that important tumour derived information is protected in ecDNA and enables the use of ecDNA from plasma as DNA source for transcription, translation and presentation in APCs, and the possibility to provide a personalized therapeutic cancer vaccination program. A personalized therapeutic cancer vaccination program may be defined as the generation of personalized vaccines which are tailored to the tumour characteristics of each patient or group of patients.

Although the description above contains a plurality of specificities, these should not be construed as limiting the scope of the concept described herein but as merely providing illustrations of some exemplifying embodiments of the described concept. It will be appreciated that the scope of the presently described concept fully encompasses other embodiments which may become obvious to those skilled in the art, and that the scope of the presently described concept is accordingly not to be limited. Reference to an element in the singular is not intended to mean "one and only one" unless explicitly so stated, but rather "one or more."

The invention claimed is:

1. A method of preparing a composition comprising tumour associated extrachromosomal circular DNA (ecDNA), comprising:
- extracting total DNA content from tumour cells of a subject;
- enriching the tumour associated extrachromosomal circular DNA (ecDNA) from the extracted total DNA content; and
- combining the tumour associated extrachromosomal circular DNA (ecDNA) with at least one of pharmaceutically acceptable component selected from buffers, salts, preservatives, carriers, adjuvants and saponins to provide the composition comprising tumour associated extrachromosomal circular DNA (ecDNA); and administering the composition comprising tumour associated extrachromosomal circular DNA (ecDNA) to the subject.

2. The method according to claim 1 further comprising a step of amplifying the enriched ecDNA.

3. A method of preparing a composition comprising tumour associated extrachromosomal circular DNA (ecDNA), comprising:
- extracting total DNA content from tumour cells of a subject;
- enriching the tumour associated extrachromosomal circular DNA (ecDNA) from the extracted total DNA content;
- delivering the enriched ecDNA to autologous antigen presenting cells ex vivo; and
- administering the autologous antigen presenting cells delivered with the enriched ecDNA to the subject.

4. The method according to claim 3, further comprising binding at least a portion of the enriched ecDNA to nanoparticles selected from polymer particles, lipid particles and liposome particles, or peptide-based delivery modalities; or microparticles selected from gold or tungsten microparticles.

5. The method according to claim 3, wherein the antigen presenting cells are dendritic cells.

* * * * *